United States Patent [19]

Kato et al.

[11] Patent Number: 5,105,455
[45] Date of Patent: Apr. 14, 1992

[54] X-RAY DIAGNOSTIC APPARATUS

[75] Inventors: Kunitaka Kato, Utsunomiya; Sukekiyo Narita; Teruomi Gunji, both of Ootawara, all of Japan

[73] Assignee: Kabushiki Kaisha Toshiba, Kawasaski, Japan

[21] Appl. No.: 603,364

[22] Filed: Oct. 26, 1990

[30] Foreign Application Priority Data

Oct. 30, 1989 [JP] Japan ................................ 1-279872
Nov. 15, 1989 [JP] Japan ................................ 1-294877

[51] Int. Cl.⁵ .............................................. H05G 1/54
[52] U.S. Cl. ....................................... 378/117; 378/95; 250/227.16
[58] Field of Search ........................ 378/95, 114, 117; 250/227.16; 340/555.590

[56] References Cited

U.S. PATENT DOCUMENTS

| | | | |
|---|---|---|---|
| 4,358,856 | 11/1982 | Stivender et al. | 378/197 |
| 4,482,890 | 11/1984 | Forbes et al. | 250/227.16 |
| 4,733,408 | 3/1988 | Beikuefner et al. | 378/117 |
| 4,969,170 | 11/1990 | Kikuchi et al. | 378/145 |

*Primary Examiner*—Janice A. Howell
*Assistant Examiner*—Don Wong
*Attorney, Agent, or Firm*—Oblon, Spivak, McClelland, Maier & Neustadt

[57] ABSTRACT

A protection cover includes a pressure responsive means mounted within the cover along its inner wall surface and which operates responsive to external forces to be exerted upon contact with a neighboring object. The protection cover is provided at a portion where physical contact may occur between any of movable or rotating component devices of an X-ray diagnostic apparatus, such as, an X-ray exposure unit or an image intensifier, and a neighboring object which is in the path of the component devices, such as, a subject or a catheter table. The protection cover may, for example, be provided at a moving end of a component X-ray diagnostic apparatus, such as, the forward end of the image intensifier, or may be mounted, instead of being mounted on a movable component device, on a neighboring object at its side facing to the movable part of the component devices, such as, a stand section of the catheter table, which lies in the path of a moving part of the X-ray radiographing component devices.

3 Claims, 3 Drawing Sheets

X-RAY DIAGNOSTIC APPARATUS

BACKGROUND OF THE INVENTION

1. Field of the Invention

This invention relates to X-ray diagnostic apparatuses and, more particularly, to an X-ray diagnostic apparatus provided with safety means which senses physical contact between component devices, such as an X-ray exposure unit and an image intensifier, and peripheral objects located in surrounding areas and which stops the operation of the X-ray diagnostic apparatus upon occurrence of such contact.

2. Description of the Related Art

An X-ray diagnostic apparatus of the type mentioned for use in medical diagnosis is known wherein a rotation arm of substantially a letter C-shaped configuration having a pair of confronting arm units is mounted on a rotating support secured to a wall or ceiling, and component members typically including an X-ray exposure unit, an image intensifier, etc. are respectively disposed on free ends of the arm units. Adjacent the arm support side of the X-ray diagnostic apparatus is placed a catheter table having thereon a lengthwisely slidable top plate on which a subject to be examined or diagnosed is placed. The rotation arm is rotatable in a horizontal direction with the rotation of the rotating support and is rotatable also about its own axis at a point at which it is mounted to the rotating support. Further, the rotatable support is vertically movable to provide for position adjustment. In the X-ray diagnostic apparatus so constructed, an X-ray diagnostic operation may take place by rotating the rotation arm in relation to the rotation of the rotating support or rotating the same about its own axis, thereby to permit the above component devices to move to a desired location around the subject lying on the top plate of the catheter.

In operating the X-ray diagnostic apparatus, it frequently occurs that the component devices, as they rotate or travel, come into contact with peripheral objects including, for example, a top plate of the catheter table, its support stand, monitoring equipment, as well as moving objects including a subject and an operator, that lie in the path of the movable component members.

Safety measurements taken in a conventional device of the type mentioned provide for contact switches in the path of moving component members, the sensor switches being operative upon occurrence of contact between them and an peripheral or neighboring object to stop or fault the operation of the rotation arm, thus attaining safety in operation and avoiding damages arising out of the contact.

The known contact switch is constructed by a tape switch attached to the rear surface of a resin or metallic cover mounted, via spring means, on a component member, such as, the forward surface of an image intensifier, and a dogg projecting from the same surface at a side opposite the tape switch, in such a manner that the tape switch and the dogg are held in connection or disconnection by external forces applied to the cover. This arrangement, however, involves the following drawbacks.

1. The drive of the switch is by a spring force, so that it is difficult to make adjustment and the operation of the switch is not stable.

2. The operation of the switch is limited regarding a direction in which forces are applied. The switch is less effective against forces that are applied in directions other than a direction in which the switch and the dogg face each other.

3. The construction of the cover having the switch is complicated and does not provide a good touch in the event a subject contacts the cover.

SUMMARY OF THE INVENTION

This invention has been achieved to remove the drawbacks above mentioned and has for its object to provide an X-ray diagnostic apparatus having sensor switch means which is capable of positively operating against external forces acting in all directions, attaining both safety in operation of the diagnostic apparatus and prevention of accidents due to contact between component members of the device and a neighboring object, and yet providing for a greatly softened touch to a moving object in the event of contact.

To achieve the foregoing object, the apparatus according to this invention provides, in an X-ray diagnostic apparatus comprising a rotation arm having a pair of mutually confronting arm units, and X-ray radiographing component devices mounted on free ends of the arm units and wherein an X-ray photographing operation takes place by rotating the rotation arm about a catheter table and thereby moving the X-ray radiographing component devices around a subject lying on the catheter table, an X-ray diagnostic apparatus further comprising an elastic protection cover or covers provided in the path of the radiographing component devices, and a pressure sensor provided within the protection cover along its inner wall surface and which is operative to terminate the movement of the rotation arm upon detection of external forces.

BRIEF DESCRIPTION OF THE DRAWINGS

The foregoing and other features and objects of the present invention and the manner of attaining them will become more apparent and the invention itself will be best understood by reference to the following embodiment of the present invention taken in conjunction with the accompanying drawings, wherein:

FIG. 1 being a front elevation schematically illustrating the construction of the apparatus;

FIG. 2 being a side view of an image intensifier, a component device used in the above apparatus;

FIG. 3 being an enlarged front elevation of a section A of FIG. 2;

FIG. 4 being a vertical cross section of an elastic optical fiber unit; and

DETAILED DESCRIPTION OF THE PREFERRED EMBODIMENTS

One embodiment of the invention will be described with reference to FIGS. 1 to 5.

Figure 1:
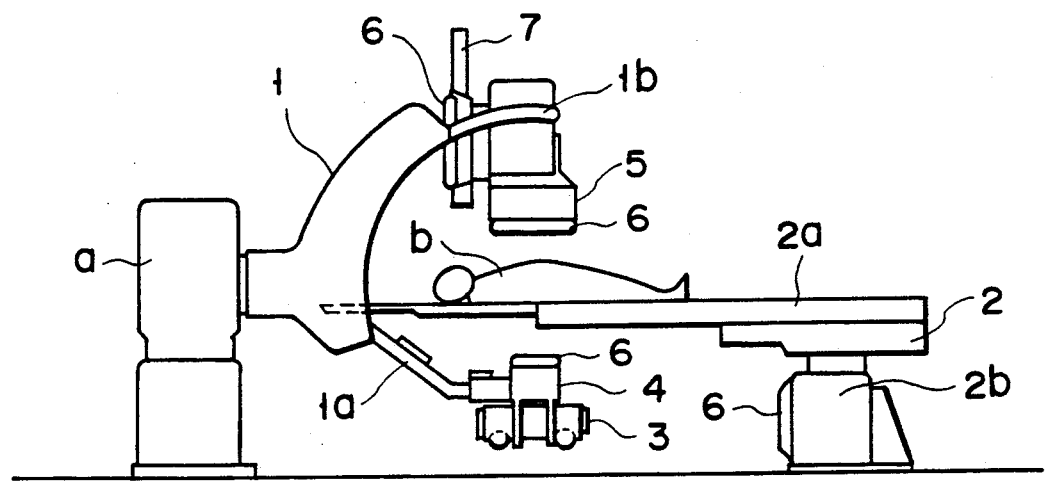
FIGS. 1 to 4 show an X-ray diagnostic apparatus according to one embodiment of the invention.

Numeral 1 in FIG. 1 denotes a rotation arm, mounted on a rotating support a installed on a floor base, and which is rotatable with the rotation of the rotating support a in a horizontal plane tangentially intersecting the axis of the rotating support a. The rotation arm itself is also rotatable about its own axis of mounting. Numeral 2 is a catheter table similarly mounted on the floor base and on which a top plate 2a on which a subject b may be placed is mounted slidably in a longitudinal direction.

The rotation arm has at its free ends a pair of confronting arm units 1a and 1b whereby the entire structure defines substantially a letter C-shaped configuration. On the forward or free ends of the arm units are respectively mounted X-ray radiographing component devices including, for example, an X-ray exposure unit having an X-ray tube 3 and a movable X-ray collimator 4 on the arm unit 1a, and an image intensifier 5 on the other arm unit 1b in the illustrated embodiment. Each of these component devices is rotatably supported with respect to one of the arm units so that its angle of inclination and a direction in which it lies may be optionally adjusted. The reference numeral 7 shows a film changer attached to the image intensifier 5.

Figure 2:
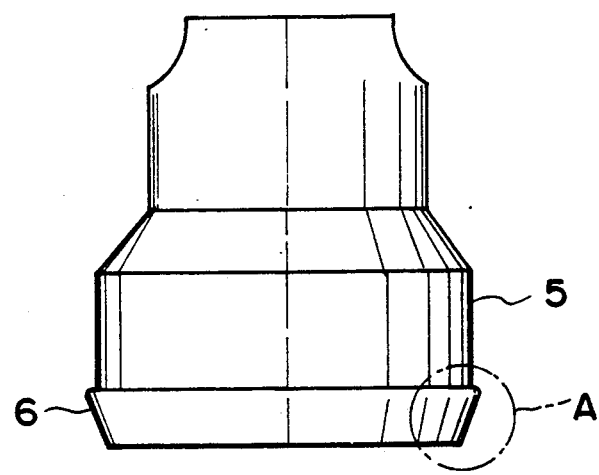

Numeral 6 is a contact sensor switch equipped for an X-ray radiographing component device, and which may be located, for example, on the forward end of the image intensifier 5 as shown in FIG. 2.

Figure 3:
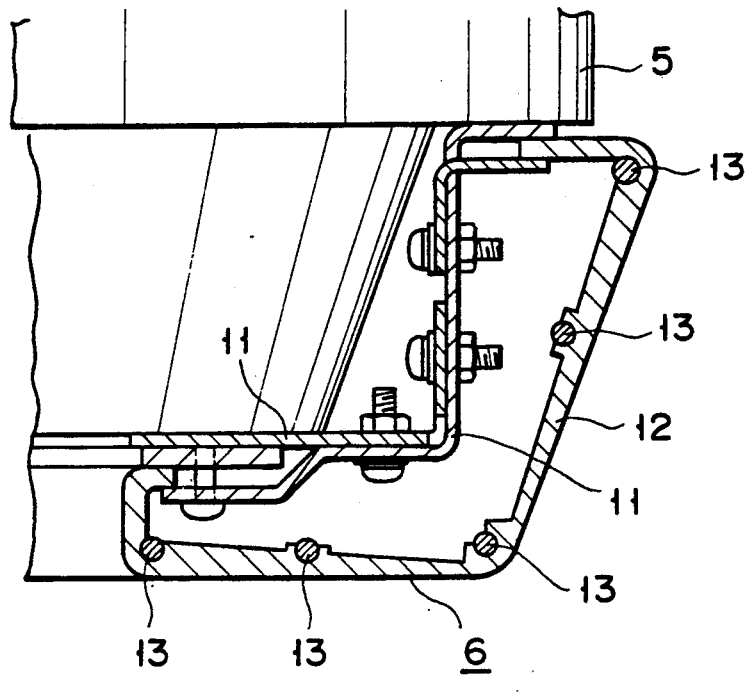

A specific arrangement of the sensor switch 2 is shown in FIG. 3 (an enlarged view of a portion A in FIG. 2). As shown, the sensor switch 2 includes a ring-shaped protection cover 12 secured at the forward circumferential edge of the image intensifier 5 via a mounting metal 11. In the inner wall surface are disposed a plurality of elastic optical fiber units 13 having flexibility, which run along the inner wall of the image intensifier 5 in the form of stripes parallel to each other in fixed spacings.

Figure 4:
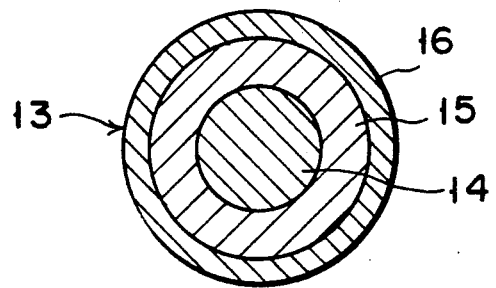

The protection cover 12 is formed of an elastic material, such as rubber. The optical fiber units 13 have, as shown in FIG. 4, a three-layer structure having a core 14 formed, for example, of silicone rubber material of a high refractive index, a clad 15 formed, for example, of silicone rubber material having a low refractive index, overlying the core 15, and a coating 16, for example, of fluoro rubber coating the outer surface of the clad 15.

Figure 5:
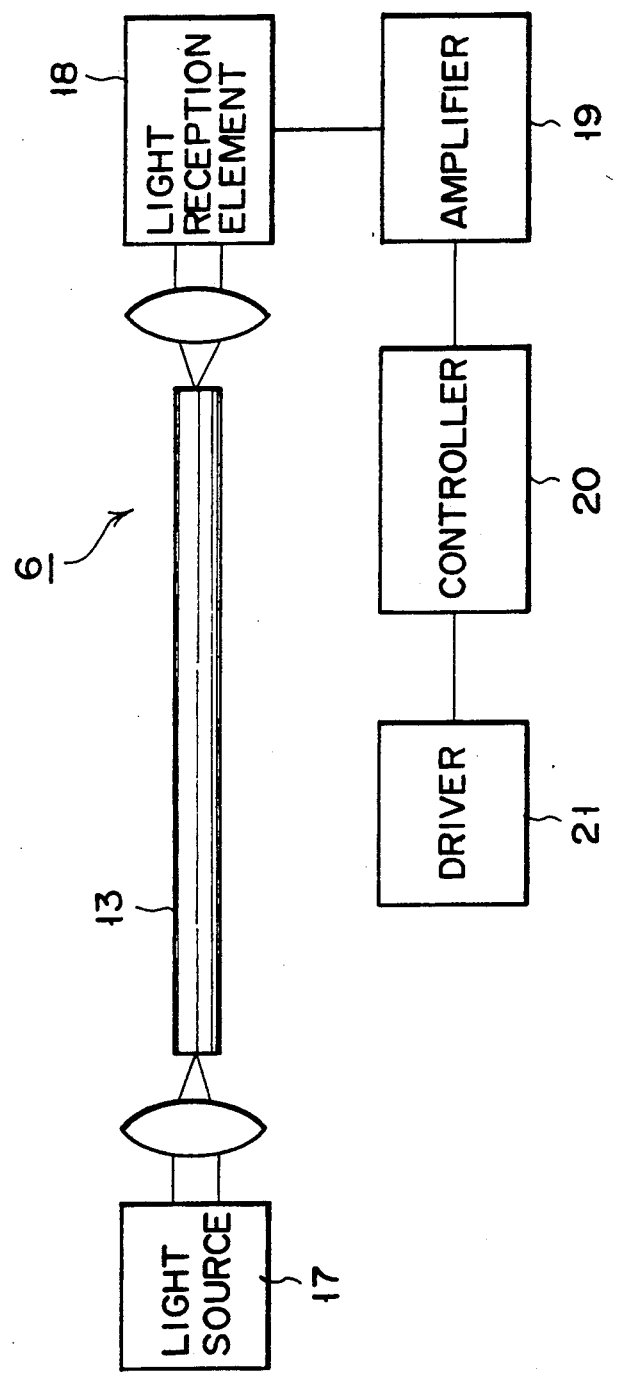
FIG. 5 is a schematic block diagram showing the function mechanism of a pressure sensor incorporating the elastic optical fiber unit of FIG. 4.

As shown in FIG. 5, the optical fiber unit 13 is connected at one end to a light source 17 and at the other end to a light reception element 18, the light source 17 and the light reception element 18 being respectively disposed via optical lens. The light reception element 18 is connected to a controller 20 and a driver 21 via an amplifier 19, so that a photoelectric conversion signal outputted by the light reception element 18 is fed to the controller 20 via the amplifier 19. An output signal from the controller 20 causes the driver 21 to be operative to drive the rotation arm 1.

A sensor switch 6 provided at the forward end of the X-ray collimator 4 of the X-ray tube 3 has the same construction as above.

When external forces are applied in the above mentioned arrangement, is applied, for example, to the protection cover 12 mounted on a forward circumferential edge of the image intensifier 5, the protection cover 12 is subjected to elastic deformation which in turn causes the optical fiber units 13 to undergo elastic deformation. This results in disordering conditions for total reflection of the fibers and decreasing the quantity of light to be transmitted. The decrease in the transmission of light is sensed by the light reception element 18 attached to one end of the respective optical fiber units 13. A photoelectrically converted output signal from the light reception element 18 is transferred to the driver 21 via the signal processing circuit elements shown in FIG. 5, thereby to stop the operation of the rotation arm. Accordingly, when any neighboring object, such as, the subject or the top plate or support platform of the catheter table is brought into contact with the forward end of the image intensifier 5 or the X-ray collimator 4, such contact is immediately sensed by the sensor switch 6 to stop the operation of the X-ray diagnostic apparatus, whereby damages due to contact between the component devices and a neighboring object may be avoided. The protection cover and the optical fiber units that have been once deformed by external forces may restore their original state so as to be ready for subsequent operation.

According to this embodiment, since the sensor switch 6 is formed by the elastic protection cover 12 and the elastic optical fiber units 13 mounted along the inner surface of the protection cover 12, an external force exerted thereon from any direction can be sensed at high sensitivity, thus providing for stable switching functions. Moreover, when the subject happens to come into contact with the protection cover, the touch is so soft that no disagreeable feeding may be generated to the subject or the operator.

Although the sensor switch 6 is provided at a forward end surface of the movable X-ray collimator 4 and of the image intensifier 5 in the foregoing embodiment, it may be provided at the forward end surface of the film changer to sense contact between it and a subject b. It may also be provided at the support stand 2 of the catheter table 2 or at any neighboring equipment or devices, such as, around monitoring equipment, not shown, suspending from the ceiling.

Further, in the foregoing embodiment, while the elastic optical fiber units 13 have been used as the pressure sensing means, similar effects and functions may be attained by mounting strain gages in the inner wall of the protection cover 12 in place of the sensor switch units in the same manner as the optical fiber units. In this case, the light reception element 18 may be replaced by conversion means which detects changes in electrical resistance due to strains and which generates electrical signals.

Additional embodiments of the present invention will be apparent to those skilled in the art from consideration of the specification and practice of the present invention disclosed herein. It is intended that the specification and examples be considered as exemplary only, with the true scope of the present invention being indicated by the following claims.

What is claimed is:

1. An X-ray diagnostic apparatus comprising:
    a rotation arm having a pair of mutually confronting arm units;
    X-ray radiographing component devices mounted on forward ends of said arm units and movable about a subject lying on a catheter table by rotating the rotation arm about the catheter table, where the X-ray radiographing component devices include an X-ray exposure unit and an image intensifier, the X-ray exposure unit being mounted on a forward end of one of the arm units, and the image intensifier being mounted on a forward end of an other of the pair of arm units;
    elastic protection covers disposed in a path of travel of the X-ray exposure unit and the image intensifier; and
    pressure sensors located along inner surfaces of the protection covers and which are operative by sensing an external force to stop a rotation of the rotation arm, wherein said pressure sensor is formed of an elastic optical fiber having flexibility, the elastic optical fiber including an elastic core having a high refractive index, an elastic clad overlying the elastic core and having a low refractive index, and a cover surrounding an outer surface of the elastic clad.

2. The X-ray diagnostic apparatus according to claim 1, wherein a film changer is provided at the image intensifier, a protection cover formed of an elastic material is disposed in the travel path of the film changer, and the pressure sensors are disposed along the inner wall surface of the protection cover disposed in the travel path of the film changer.

3. The X-ray diagnostic apparatus according to claim 1, wherein a protection cover formed of an elastic material is disposed at a contact portion of the catheter table which has a possibility of contacting the X-ray radiographing component devices, and the pressure sensors are mounted along an inner wall surface of the protection cover disposed at a contact portion of the catheter table.

* * * * *